United States Patent [19]
Koenen Myers et al.

[11] Patent Number: 5,816,676
[45] Date of Patent: Oct. 6, 1998

[54] WORK GLOVE AND ILLUMINATOR ASSEMBLY

[76] Inventors: Howard P. Koenen Myers, 228 Commercial St. #521, Nevada City, Calif. 95959; Raymond W. Trow, 4417 Lanza Ln., Stockton, Calif. 95207

[21] Appl. No.: 603,907

[22] Filed: Feb. 22, 1996

Related U.S. Application Data

[60] Division of Ser. No. 165,408, Dec. 10, 1993, Pat. No. 5,535,105, which is a continuation-in-part of Ser. No. 926,164, Aug. 5, 1992, Pat. No. 5,283,722.

[51] Int. Cl.$^6$ .................................................. G03B 15/02
[52] U.S. Cl. ................................ 362/8; 362/103; 362/32
[58] Field of Search ...................................... 348/359, 376; 600/182; 362/3, 7, 8, 16, 32, 804, 103

[56] References Cited

U.S. PATENT DOCUMENTS

| | | | |
|---|---|---|---|
| 455,972 | 7/1891 | Oudin et al. . | |
| 914,975 | 3/1909 | Radley . | |
| 1,173,269 | 2/1916 | Heidemann . | |
| 1,553,860 | 9/1925 | Hopper . | |
| 3,638,011 | 1/1972 | Bain et al. . | |
| 3,811,684 | 5/1974 | Tredway, Sr. | 273/183 B |
| 4,415,905 | 11/1983 | Hattori et al. | 362/32 |
| 4,422,131 | 12/1983 | Clanton et al. | 362/186 |
| 4,718,406 | 1/1988 | Bregman et al. | 600/182 X |
| 4,757,426 | 7/1988 | Scheller et al. | 362/20 |
| 4,823,244 | 4/1989 | Alaybayoglu et al. | 362/194 |
| 4,887,194 | 12/1989 | Fields | 362/105 |
| 4,970,631 | 11/1990 | Marshall | 362/105 |
| 4,974,094 | 11/1990 | Morito | 358/225 |
| 5,003,434 | 3/1991 | Gonser et al. | 362/32 |
| 5,086,378 | 2/1992 | Prince | 362/103 |
| 5,124,892 | 6/1992 | Lambert | 362/103 |
| 5,283,722 | 2/1994 | Koenen et al. | 362/103 |
| 5,305,736 | 4/1994 | Ito | 600/182 X |

FOREIGN PATENT DOCUMENTS

| | | |
|---|---|---|
| 1736426 | 5/1992 | U.S.S.R. . |
| 1736426A1 | 5/1992 | U.S.S.R. . |
| 2107571 | 5/1983 | United Kingdom . |

OTHER PUBLICATIONS

Advertisement, PS, "Thimble Scope", p. 12, Apr. 1996.
Article, Plastics Designs Compete, *Machine Design,* Jul. 9, 1993, p. 12.

*Primary Examiner*—Stephen F. Husar
*Attorney, Agent, or Firm*—David A. Farah, M.D.; Sheldon & Mak

[57] ABSTRACT

A work glove and illuminator assembly is provided. An illuminator is securely mounted on the glove and oriented to project a light beam distally of the glove toward the work surface when the glove is in use. The illuminator may have a self-contained light source, or utilize fiber optic-transmitted light from a light source remote from the glove. The assembly may comprise a laser generator or may utilize a fiber optic-transmitted laser light from a laser generator remote from the glove. The assembly may further comprise a video camera operably attached to a video receiver, a video monitor and/or a video recorder. In one embodiment of the invention, the illuminator is disposed within the interior of the glove and projects a beam of light through a glove tip which is translucent or transparent. The assembly is particularly suitable for use by health care professionals when examining or operating upon an anatomical part of a patient.

8 Claims, 5 Drawing Sheets

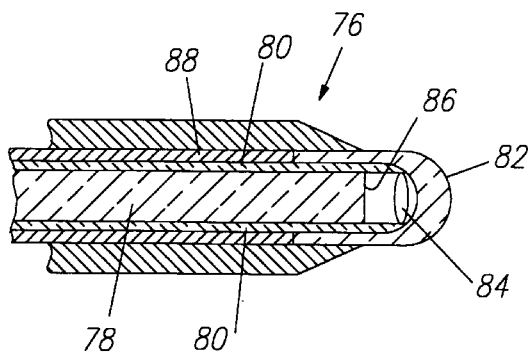
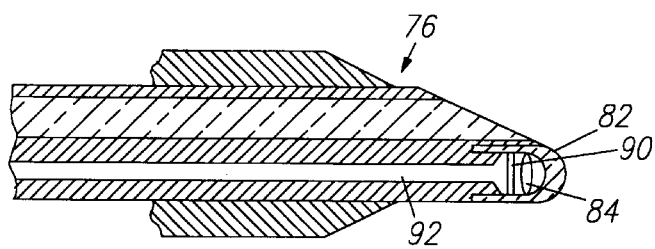
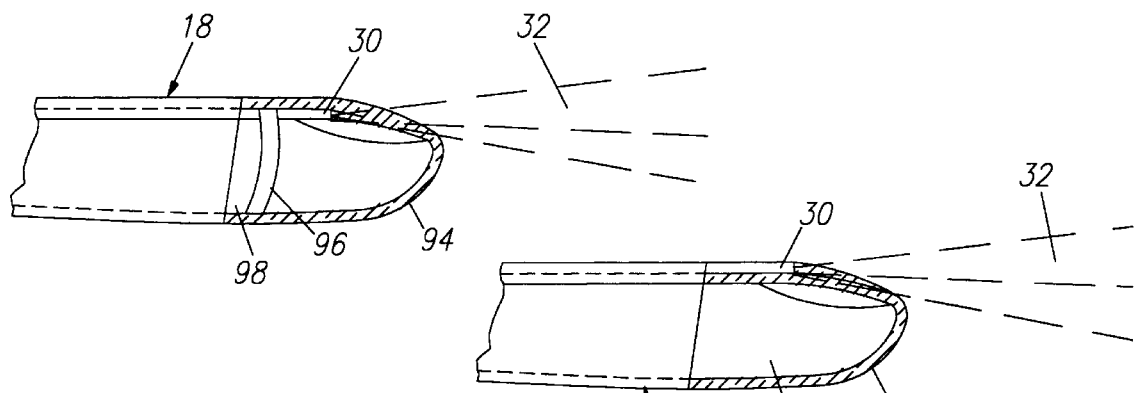
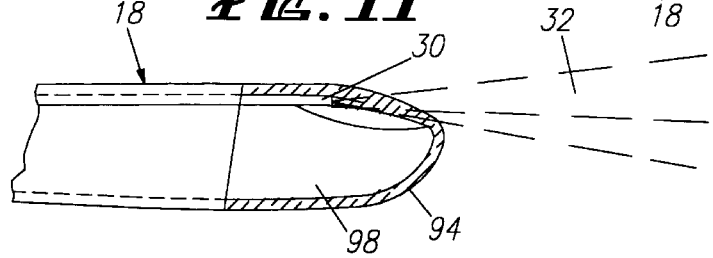

WORK GLOVE AND ILLUMINATOR ASSEMBLY

This application is a divisional of U.S. patent application Ser. No. 08/165,408, titled WORK GLOVE AND ILLUMINATOR ASSEMBLY, filed Dec. 10, 1993, now U.S. Pat. No. 5,535,105, which is a continuation-in-part of U.S. patent application Ser. No. 07/926,164, filed Aug. 5, 1992, titled SURGICAL-TYPE GLOVE AND ILLUMINATOR ASSEMBLY, now U.S. Pat. No. 5,283,722.

FIELD OF THE INVENTION

This invention relates generally to protective gloves such as the type worn by health care professionals when examining or operating upon patients, and more particularly, to gloves incorporating an illuminator for projecting light toward the work surface being examined or operated upon.

BACKGROUND

As was discussed in my previous application, now U.S. Pat. No. 5,283,722, for workers in the health care field, electronic parts assembly field and other fields requiring close work, illumination of the work area is a considerable problem. For example, when examining or operating upon an anatomical part of a patient, physicians, dentists and veterinarians will usually have available to them several different forms of lighting for illuminating their field of examination or operation. These include natural light entering the room through windows, overhead general room lighting, and directable high intensity lamps in fairly close proximity to the patient. Oftentimes, circumstances will require that these various sources of illumination be supplemented by a spotlighting type of illumination more specifically focused toward the particular body part being examined or operated upon.

One approach for providing such spotlighting has been to incorporate illumination devices in combination with the worker's tools and instruments. This type of approach is described, for example, in U.S. Pat. No. 4,823,244, issued Apr. 18, 1989, and U.S. Pat. No. 5,003,434, issued Mar. 26, 1991. In the devices described in these patents, light is transmitted through the bore of the instrument itself or its handle, and projected toward the work surface through the distal tip of the instrument or distal ports in the handle. The light source may be, for example, a battery-powered lamp either housed entirely within the bore of the instrument or handle or detachably connected thereto. Alternatively, an optical fiber cable may be used for transmitting light to the bore of the instrument from a light source remote from the instrument.

The devices described in the above patents have certain inherent limitations, however. The relatively small size of the light output ports and their close proximity to the work surface, limit the work surface area that can be effectively illuminated by the projected light beam and permit little variance in the angle of projection of the light beam. Furthermore, since these devices rely upon the instrument or its handle being of hollow construction, this approach lacks universal applicability for use with all types of close work tools.

In my prior application, now U.S. Pat. No. No. 5,283,722, I proposed a surgical-type glove and illuminator assembly wherein the illumination means comprised a light housing mounted on the exterior surface of the glove and one or more fiber optics terminating in a light distribution lens affixed to one or more of the fingers of the glove. This particular device has been found to significantly reduce the problem of illuminating close-up work. However, this device does not provide any way for the work area to be projected onto a display screen and/or for the work progress to be recorded onto tape or other permanent medium. Also, the device described in my prior application requires a specially-made glove wherein the illumination means is physically attached to the glove. Such attachment can be somewhat costly.

Accordingly, there remains a need for an illumination device which will allow the illumination of close-up work and which can project the work area onto a display screen which can also provide a recorded record of the work progress. There is a further need for an illumination device for illuminating and displaying close-up work, and for providing other components and functions at the users fingertips in close proximity to a glove with a connection at some point at the wrist or remote of the glove. Still further, there is a need for an illumination device which is significantly less expensive to manufacture than previous illumination devices.

SUMMARY

The invention satisfies these needs. The invention is a glove and illuminator assembly comprising a glove having a plurality of fingers. An illumination means is securely mounted on or in close proximity to the glove and oriented to project a light beam distally of the glove towards the work surface when the glove is in use.

In one embodiment of the invention, the assembly further comprises a laser beam generator which can be used to operate directly at the work surface.

In another embodiment, the assembly further comprises a video camera. The video camera is operably attached to a video display screen and/or a video recording device.

In other embodiments, radio or microwave controlled components needed in surgery can be added to the glove.

In still another embodiment, at least one finger tip of the glove is translucent or transparent and the illumination means is disposed within the glove and directed to project a light beam through the wall of the fingertip to illuminate the work surface. In this embodiment, the illumination means can be disposed proximate to the interior surface of the glove but does not need to be attached to the glove. The illumination means can be separately attached to the fingers of the user, such as by elastic bands. Where the glove is made of a close fitting resilient material, such as latex, the illumination means can be held fast to the hand of the user by the resilient pressure exerted by the walls of the glove.

The invention has been found to be useful in a wide variety of close work, such as in surgical operations and other close-in medical work and in the assembly and repair of small mechanical and electronic components. Therefore, embodiments can use different materials for the glove, such as cotton, leather and neoprene. The invention is simple, inexpensive and easy to use.

DESCRIPTION OF DRAWINGS

These and other features, aspects and advantages of the present invention will become better understood with reference to the following description, appended claims and accompanying drawings where:

FIG. 8 is a detailed cross-sectional side view drawing of the distal end of a fiber optic scope useful in the embodiment of the invention shown in FIG. 7;

FIG. 9 is a detailed cross-sectional side view of a second distal end of a fiber optic scope useful in the embodiment illustrated in FIG. 7;

FIG. 10 is a side view of a finger tip portion of an embodiment of the invention comprising a translucent finger tip, illustrating the use of an elastic band to attach the illumination means to the finger of the user;

FIG. 11 is a side view of a finger tip portion of an embodiment of the invention comprising a translucent finger tip, illustrating the embodiment of the invention wherein the glove tightly adheres the illumination means to the finger of the user;

FIG. 12 is a side view of a finger tip portion of an embodiment of the invention comprising a translucent finger tip, illustrating an embodiment of the invention wherein the illumination means is physically attached to the inside wall of the glove;

DESCRIPTION OF THE INVENTION

Figure 1:
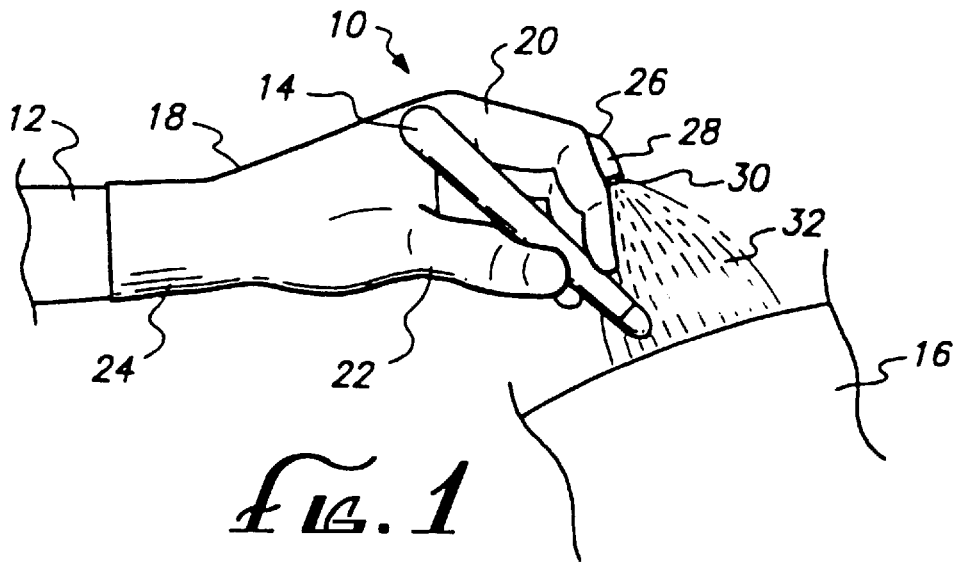
FIG. 1 is a side elevational view of a surgical-type glove and illuminator assembly in accordance with the present invention, being worn over the hand of a health care professional operating upon an anatomical part of a patient or a worker manipulating mechanical or electrical parts.

Referring now to the drawings, FIG. 1 illustrates a glove and illuminator assembly 10 in accordance with the present invention. The assembly 10 is shown being worn over the hand of a surgeon or worker 12 holding an instrument 14 while operating upon an anatomical part of a patient or other work surface 16.

The assembly 10 includes a glove 18, such as a surgical-type or workers glove of standard construction well-known in the art, formed of thin rubber or flexible plastic, or other material suitable for the job at hand, and having an interior hand chamber, a distal fingers portion 20, an intermediate metacarpal portion 22, and a proximal wrist portion 24. An illuminator 26, having a light housing 28 terminating in a distally facing light output lens 30, is securely mounted on the glove 18, and oriented to project a light beam 32 distally of the glove 18 toward the anatomical part or work surface being operated upon.

Figure 2:
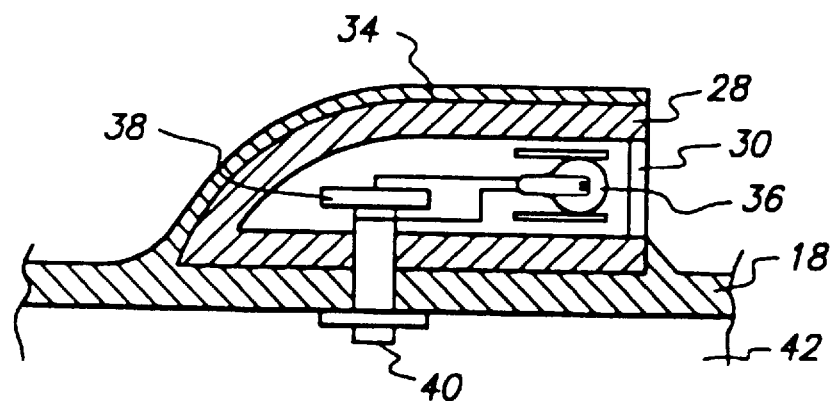
FIG. 2 is an enlarged fragmentary side elevational view of one embodiment of the assembly illustrated in FIG. 1, with portions broken away and sectioned to illustrate certain details of construction.
Figure 3:
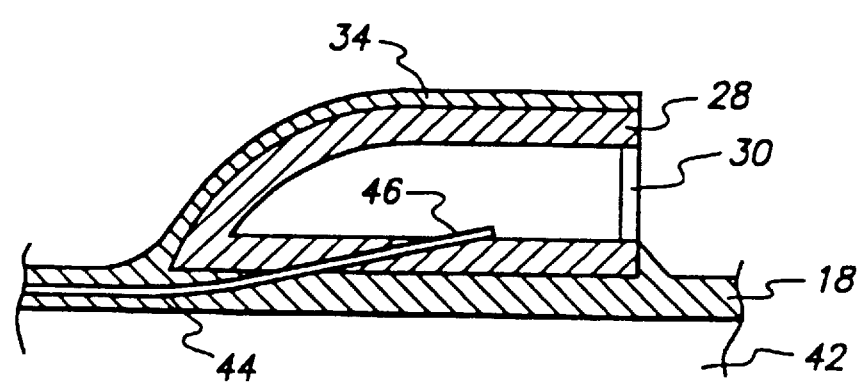
FIG. 3 is an enlarged fragmentary side elevational view similar to FIG. 2, but showing an alternative embodiment of the assembly illustrated in FIG. 1.

In order to ensure against accidental disengagement of the illuminator 26 from the glove 18, the illuminator should be mounted on the glove in a secure fashion. Means for accomplishing this are illustrated in FIGS. 2 and 3. As shown, an encasement sheath 34 is formed integrally with the glove 18 and covers the housing 28 without obstructing the lens 30. This type of construction is particularly suitable for use with rubber gloves manufactured by dipping a mold into liquid latex, removing the mold from the liquid, and allowing the latex to dry. Insertion between successive latex dippings of the illuminator 26 with its lens 30 masked, and removal of the masking after final drying, will result in the integrally formed encasement sheath 34 shown in FIGS. 2 and 3. A similar effect can be achieved, but without the encasement sheath being formed integrally with the glove, by shrink-wrapping the illuminator 26 onto the glove 18 with thin plastic film which, if transparent, can also cover the lens 30.

FIG. 2 illustrates one embodiment of the assembly 10 shown in FIG. 1, wherein the light source for the illuminator 26 is self-contained within the light housing 28. In this embodiment, an incandescent bulb 36 and a battery 38 for powering the bulb, are both carried within the housing 28. The bulb 36 is operated by a push button switch 40 located on the underside of the housing 28 and which may or may not project through the glove 18. In this manner, the switch is operable by finger movement of the wearer of the glove.

FIG. 3 illustrates an alternative embodiment of the assembly 10 shown in FIG. 1, utilizing fiber optics to transmit light to the illuminator 26 from a light source, including a laser light source, remote from the glove. In this embodiment, at least one optical fiber 44 has a length thereof embedded within the material of the glove 18 and, as shown in FIG. 3, has its distal end 46 extending through the wall of the light housing 28 into communication with the interior of the housing and pointed toward the light output lens 30.

Figure 4:
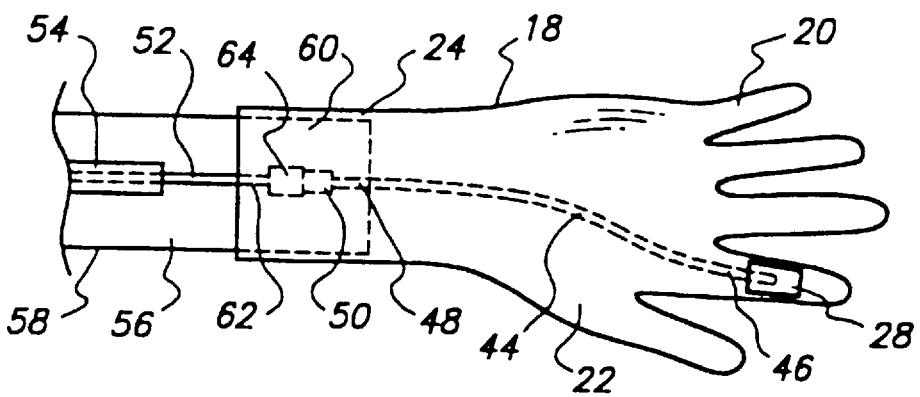
FIG. 4 is a top plan view of the assembly illustrated in FIG. 1 in flattened non-operating form, and further illustrating the alternative embodiment of FIG. 3.
Figure 5:
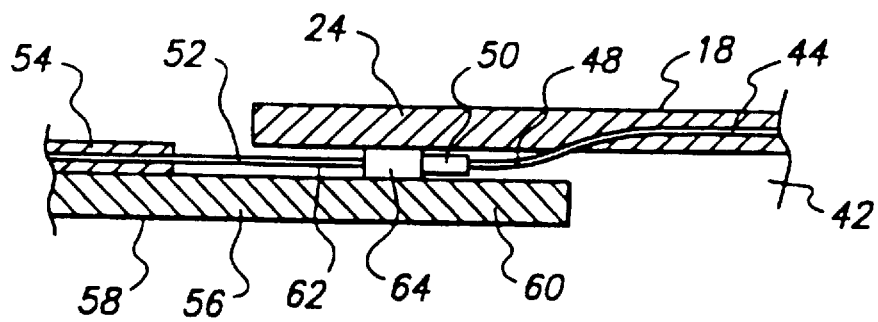
FIG. 5 is an enlarged fragmentary side elevational view of the assembly illustrated in FIG. 4, with portions broken away and sectioned to illustrate certain details of construction.

As shown in FIGS. 4 and 5, the length of optical fiber 44 embedded within the material of the glove 18, extends lengthwise from the housing 28 through the metacarpal portion 22 and into the wrist portion 24 of the glove 18. The proximal end 48 of the optical fiber 44 exits from the glove material into the interior 42 of the glove along the wrist portion 24, and terminates along the wrist portion 24 in a fiber optic coupler 50. Through the coupler 50, the optical fiber 44 is operably coupled to a fiber optic path leading from a remote light source, including a laser light source (not shown), such as an electrically or battery powered lamp, enabling transmission of light from the light source to within the housing 28.

Particularly when the assembly of the present invention is being utilized in a surgical environment, but also with mechanical applications, a gown or jumpsuit with wrist-length sleeves will normally be worn over the body of the user. Such surgical-type gowns or jumpsuits are of standard construction well-known in the art, and can be conveniently modified so as to be particularly suitable for use in conjunction with the fiber optics embodiment of the assembly of the present invention employing an optical fiber cable leading from the remote light source. The modification involves providing the gown or jumpsuit with an attached casing through which the optical fiber cable can be suitably threaded. The casing extends along the sleeve of the gown or jumpsuit from a point adjacent to the wrist end of the sleeve, up the sleeve, over the shoulder and down the back of the gown or jumpsuit, and is secured to the gown or jumpsuit along its entire length by suitable fastening means, such as stitching or adhesive. The use of such a casing-modified surgical-type gown or jumpsuit in conjunction with the fiber optics embodiment of the assembly of the present invention enables an optical fiber cable to be suitably threaded through the casing of the gown or jumpsuit so that it exits from the casing at its proximal end along the back of the gown or jumpsuit and at its distal end adjacent to its coupling location with the coupler 50 of the assembly of the present invention. This type of arrangement facilitates the coupling action while maintaining a sterile field, and also facilitates keeping the optical fiber cable out of the way of the surgeon or worker while working with the glove and illuminator assembly.

The use of the casing-modified surgical-type gown or worker jumpsuit described above in conjunction with the fiber optics embodiment of the assembly of the present invention, is illustrated in FIG. 4. An optical fiber cable 52 leading form a remote light source (not shown) is threaded through and carried within a casing 54 secured along a sleeve 56 of a surgical-type gown or worker jumpsuit 58 adapted to be worn over the body of the user, with the wrist end 60 of its sleeve 56 extending to the wrist of the user, and the wrist portion 24 of the glove 18 extending over the wrist end 60 of the sleeve 56. The distal end 62 of the optical fiber cable 52 exits from the casing 54 adjacent the wrist end 60 of the sleeve 56, and terminates in a coupler 50 adapted for coupling with the coupler 50 at a coupling location overlying the wrist end 60 of the sleeve 56. As shown in FIGS. 4 and 5, the coupling location directly overlies the wrist end 60 of the sleeve 56, and is covered by the wrist portion 24 of the glove 18. In this embodiment, the wrist portion 24 is rolled over on itself during the coupling action, and then rolled back after coupling has been effected.

Figure 6:
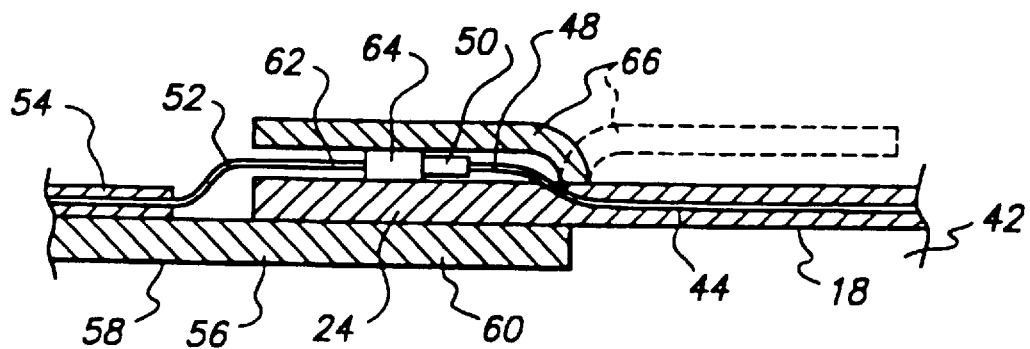
FIG. 6 is an enlarged fragmentary side elevational view similar to FIG. 5, but showing a modification of the embodiment illustrated in FIGS. 4 and 5.

FIG. 6 illustrates a modification of the embodiment shown in FIGS. 4 and 5. In the FIG. 6 modification, the proximal end 48 of the optical fiber 44 exits from the glove material along the wrist portion 24, but exteriorly of the glove body, so that the coupling location between the couplers 50 and 64 overlies the wrist portion 24 of the glove 18 as well as the wrist end 60 of the sleeve 56. With this modification, the assembly is further provided with a cuff 66 attached to the exterior of the glove 18 so as to be pivotable between a distally extending position (shown in broken lines) exposing the coupling location, and a proximally extending position (shown in solid lines) covering the coupling location. The cuff 66 is in the distally extending position during the coupling action, and then pivoted to the proximally extending position after coupling has been effected.

There may be times when a surgeon or worker encounters an unexpected emergency and needs to don a glove and illuminator assembly without changing to the surgical gown or jumpsuit where a fiber optic cable has been threaded through the gown or jumpsuit. In this case, another embodiment of the glove includes a fiber optic cable which exits the glove on the exterior surface with long fiber optic cables with the coupling, not at the wrist portion of the glove, but only at the remote light source itself (not shown). The fiber optic cable could be allowed to dangle freely or be adhered to the surgeon's or worker's arm using straps of various construction.

Figure 7:
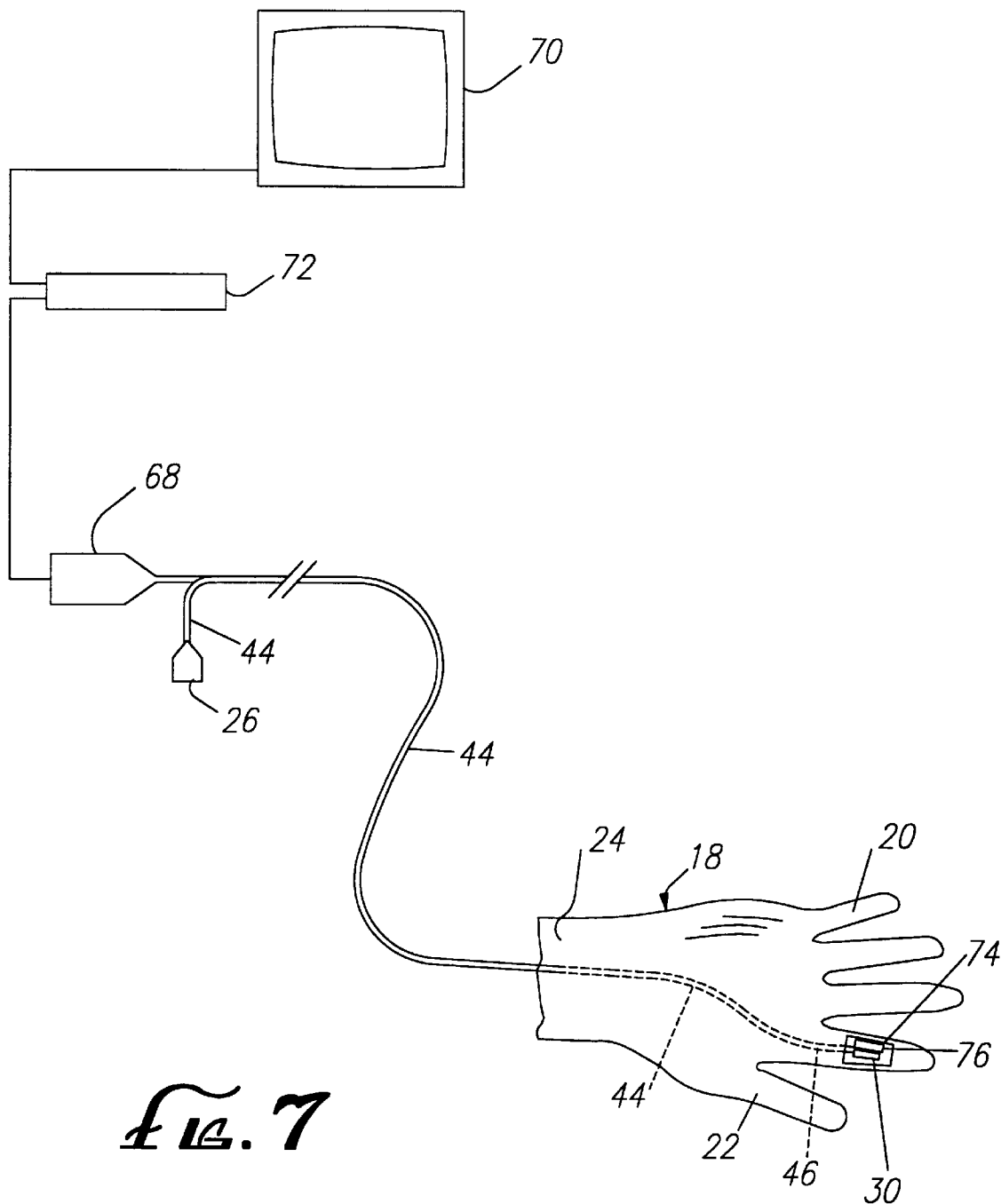
FIG. 7 is a top view and schematic diagram illustrating an embodiment of the invention comprising video monitoring equipment.

Referring to FIG. 7, a schematic diagram (not to scale) of an embodiment of the invention incorporating a video camera 68, video monitor 70 and video recorder 72 is shown. As illustrated therein, a fiber optic scope 74 is disposed adjacent to a light source out lens 30. The output lens 30 receives light from a remote light source 26 which provides sufficient light to the work surface to adequately illuminate the region surrounding the proximal end 76 of the scope 74 so that an image of adequate intensity and contrast may be received at the proximal end 76 of the scope 74. Also at the end of the scope 74, the video camera 68 with appropriate lensing to convert the image at the associated end of the fiber optic bundle to a video signal for display on video monitor 70.

The scope 74 and particularly the distal end thereof 76 may take various forms. By way of example, one relatively simple form for the distal end 76 of the scope 74 is schematically illustrated in FIG. 8. Here the fiber optic bundle is shown as two portions, mainly a central portion 78 carrying the image focused onto the proximal end thereof to the opposite end of the bundle for pickup by the video camera 68, and a circumferential portion 80 for carrying light from the light source 26 (See FIG. 7) through the dome-shaped transparent cap 82 to illuminate the surrounding tissue or working surface. The image of the illuminated work surface is focused by a lens 84 onto the end 86 of the central portion 78 of the fiber optic bundle, the design and optical characteristics of the cap 82 also being important in the imaging system. In general the tip of the fiber optic bundle, cap 82, lens 84 etc. will be a rigid assembly, though the remainder of the fiber optic bundle down to a position adjacent the opposite end thereof will in general remain flexible, the same in general being covered with a flexible sheath 88 extending from cap 82 over most of the remaining scope length.

The light source 26 (See FIG. 7) may be a conventional light source for such purposes and, for that matter, the size of the fiber optic elements used for carrying the light to the distal end 76 of the scope 74 may be larger than the fiber optic elements in the central section 78 (See FIG. 8) of the scope, because the fiber optic elements in the central section 78 should be as small as reasonably practical to provide good resolution in the image picked up by the video camera 68 and displayed on the video monitor 70. In that regard, with respect to lighting, solid state video cameras have excellent sensitivity, and if necessary, image repetition rates may be purposely reduced to increase the sensitivity of the camera. If desired, computer enhancement of the video image can be incorporated. Finally, for training purposes, insurance records, malpractice defense or merely later reference, a video recorder 72 may be used to video tape the entire procedure.

In the embodiments of the invention illustrated in FIGS. 7 and 8, the fiber optic bundle is used to convey an image on an image plane adjacent the proximal end of the scope to the opposite end of the scope for pickup by an appropriately lensed video camera. It is possible, however, to provide a video sensor array small enough and with adequate resolution to be useful in the proximal end of the scope. Thus, as shown schematically in FIG. 9, a video sensor array 90 is placed at the image plane at the proximal end of the scope, which sensor array is coupled with the remainder of the video camera electronics through a cable 92 attached thereto. In that regard, the overall system of such embodiment generally appears as shown in FIG. 7, camera 68 as described with respect to the prior embodiments of the invention now comprising the camera electronics, timing circuits, etc., but with the sensor array itself being removed therefrom and connected by way of cable 92 as hereinbefore described. In such an arrangement, reduced resolution and perhaps reduced frame rates may have to be used, using current technology, though the camera electronics could easily include a frame buffer so that the resulting image could be displayed on a conventional video monitor, recorded on a conventional VCR, etc.

FIGS. 10–12 illustrate embodiments of the invention in which the illumination output lens 30 is disposed on the interior of the glove where the polished end of the fiber optic cable itself acts as a light output lens. In these embodiments, the glove 18 has a finger tip 94 made of a material which is at least translucent, preferably substantially transparent. The illumination means output lens 30 is disposed proximate to the translucent finger tip 94 and light 32 from the output lens 30 is projected through the translucent finger tip 94 distally of the glove 18 to the work surface. The translucent finger tip 94 may be made of latex or it may be made of other materials which are at least translucent. A preferred material is a clear vinyl or other flexible plastic material which is substantially transparent.

FIG. 10 illustrates an embodiment of the invention 10 in which the illumination means output lens 30 is tightly affixed to the finger 98 of the user 12 by a resilient or adjustable band 96. Other methods of affixing the illumination means to the finger 98 can also be used.

FIG. 11 illustrates an embodiment of the invention 10 in which the glove 18 is a tight fitting glove made of a resilient material such as latex. In this embodiment, the illumination means output lens 30 can be held firmly against the user's finger 98 by the resilient pressure of the glove material alone.

FIG. 12 illustrates an embodiment of the invention 10 in which the illumination means output lens 30 is physically attached to the glove and light from the illumination means is projected outwardly through the translucent finger tip 94 of the glove 18 to a work surface distal to the glove.

Figure 13:
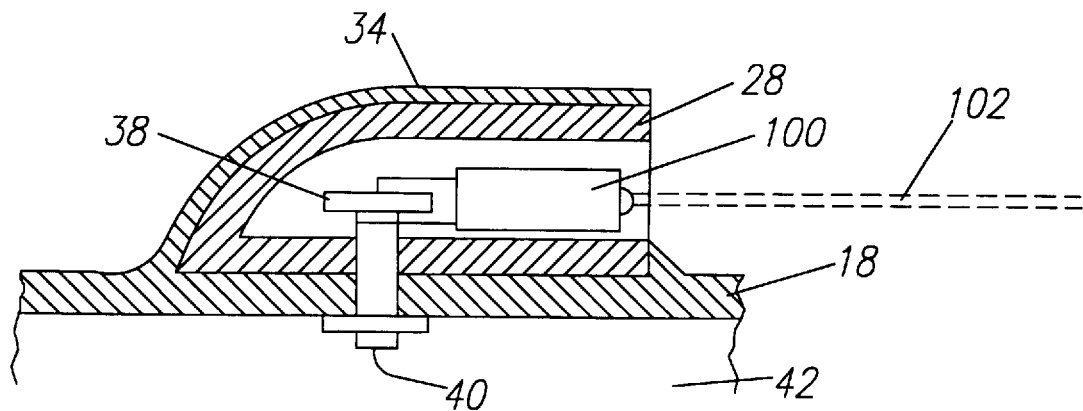
FIG. 13 is an enlarged fragmentary side elevational view of an embodiment of the invention wherein the illumination means is a laser beam generator, similar to FIG. 2.
Figure 14:
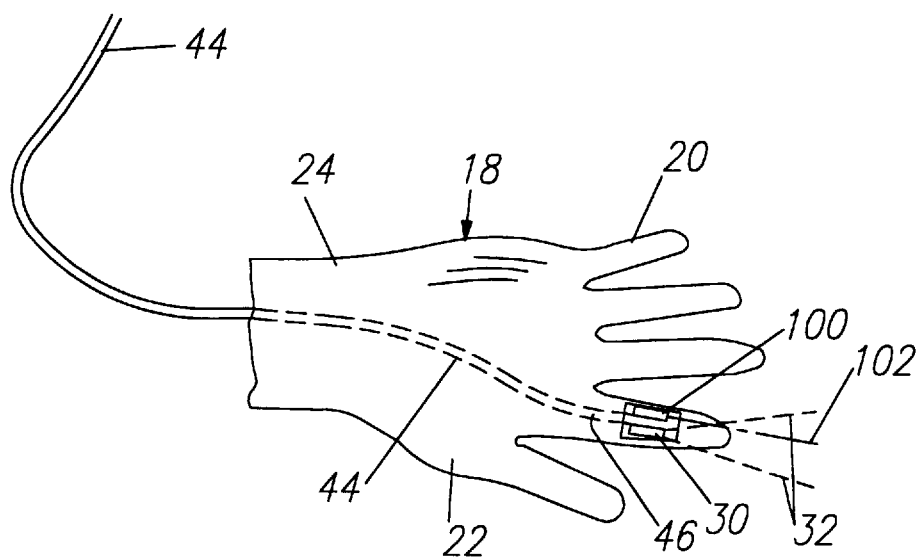
FIG. 14 is top plan view of an embodiment of the invention comprising a laser beam generator in combination with separate illumination means.

FIG. 13 illustrates an embodiment of the invention in which the illumination means is replaced with a laser beam generator 100. FIG. 14 illustrates a hybrid embodiment in which a laser beam generator 100 is disposed adjacent to an illumination means output lens 30 of the type described above. In this embodiment, the work surface is illuminated by a light beam 32 emanating from the output lens 30, while the work surface is operated upon by a laser beam 102 emanating from the laser beam generator 100.

Other components can be added to the glove illuminator assembly to create a glove illuminator component assembly. The component compartment housing can be placed near the distal aspect of at least one finger. The component-environmental interface will contain output structures for the various components. These components can include one or more fiber optic cables for light transmission, including incandescent light, laser light and images for video conversion, one or more biochemical probes, one or more microtubules and one or more environmental sampling means. These components may require the direct connection to other electronic and mechanical devices through a communication network made of fibrous material. The fibrous communication network is contained in a special connector composed of two pieces, the proximal component connector and the distal component connector between the glove portion of the fibrous communication network and the gown portion of the fibrous communication network. Also, certain functions of the components can be radiowave or microwave controlled.

Although the present invention has been described in considerable detail with reference to certain preferred versions, many other versions should be apparent to those skilled in the art. Therefore, the spirit and scope of the appending claims should not necessarily be limited to the description of the preferred versions contained herein.

What is claimed is:

1. A surgical-type glove and illuminator assembly comprising:

(a) a surgical-type glove having a distal fingers portion, an intermediate metacarpal portion and a proximal wrist portion, the glove being adapted to be worn over the hand of a user when examining or operating upon a work surface;

(b) an illumination means securely mounted on the fingers portion of the glove and oriented to project a light beam distally of the glove toward the work surface when the glove is in use; and (c) a video camera connected to the illumination means, and adapted to receive reflected light distally of the glove.

2. The assembly of claim 1 further comprising a video recorder connected to the video camera, and adapted to record signals received from the video camera.

3. The assembly of claim 1, wherein the angle of projection of the light beam is controllable by finger movement of the wearer.

4. The assembly of claim 1, wherein the illumination means comprises a light housing terminating in a distally facing light output lens.

5. The assembly of claim 4, wherein the illumination means is secured to the topside of the glove by an encasement means covering the housing without obstructing the lens.

6. The assembly of claim 5, wherein the encasement means is formed integrally with the glove.

7. The assembly of claim 4, wherein the illumination means includes a self-contained battery-powered light source carried within the housing, and switch means carried on the exterior of the housing for operating the light source.

8. A glove, illuminator and video assembly comprising:

(a) a glove defining an inside hand chamber and having a plurality of fingers;

(b) illumination means comprising a light generator and a light projector, wherein the light projector is securely mounted to one of the fingers of the glove and is oriented to project a light beam distally of the glove and wherein the light generator is connected to the light projector; and (c) a video camera connected to the light projector and oriented to receive light reflected from a work surface distal of the glove.

* * * * *